US006879394B2

(12) United States Patent
Amblard et al.

(10) Patent No.: US 6,879,394 B2
(45) Date of Patent: Apr. 12, 2005

(54) MULTI-PHOTON IMAGING INSTALLATION (75) Inventors: François Amblard, Paris (FR); Xavier Sastre-Garau, Vincennes (FR); Sylvie Robine, Vanves (FR)

(73) Assignees: Institut Curie, Cedex (FR); Centre National de la Recherchie Scientifique, Cedex (FR)

( * ) Notice: Subject to any disclaimer, the term of this patent is extended or adjusted under 35 U.S.C. 154(b) by 35 days.

(21) Appl. No.: 10/441,027

(22) Filed: May 20, 2003

(65) Prior Publication Data

US 2004/0004194 A1 Jan. 8, 2004

Related U.S. Application Data (63) Continuation of application No. PCT/EP01/14403, filed on Nov. 20, 2001.

(30) Foreign Application Priority Data

Nov. 20, 2000 (EP) .............................................. 00403238

(51) Int. Cl.$^7$ ......................... G01N 21/64; G01N 21/65
(52) U.S. Cl. ....................................... 356/301; 356/318
(58) Field of Search ................................ 356/318, 417, 356/301; 250/458.1, 459.1, 461.1, 461.2

(56) References Cited

FOREIGN PATENT DOCUMENTS

| WO | WO 90 06718 A | 6/1990 |
|---|---|---|
| WO | WO 97 11355 A | 3/1997 |

*Primary Examiner*—F. L. Evans
(74) *Attorney, Agent, or Firm*—Birch, Stewart, Kolasch & Birch, LLP (57) ABSTRACT

An installation is provided for multi-dimensional non-linear imaging of a material comprising intrinsic chromophores, using laser scanning. This installation comprises i) at least one source (115) of time stamp pulses of synchronized photons, ii) means (12–14) for locally focusing the pulses on a material to cause its intrinsic chromophores to absorb groups of at least two synchronized photons to produce response photons, iii) means (22, 40, 53) for directing the response photons to at leat one collecting zone, iv) means (30–34) for collecting the response photons in the collecting zone(s) whatever their energy, v) processing means for converting the collected photons into data at least representative of their number and storing them in correspondence with at least the time stamp pulses that cause the material to produce the response photons, vi) means for scanning (11, 20) the pulses through a chosen area of the material, and vii) means for delivering from said data stored an image representative of said material chosen area, with a sub-millimeter resolution, and in function of the respective time stamp pulses of data.

51 Claims, 3 Drawing Sheets

MULTI-PHOTON IMAGING INSTALLATION

This application is a continuation of PCT/EP01/14403 filed Nov. 20, 2001.

FIELD OF THE INVENTION

The invention relates to the field of biological material imaging with the help of time stamp pulses of synchronized photons.

This invention more particularly relates to installations and methods for imaging the intrinsic non-linear optical response of biological samples, in vivo or in vitro, for example, for the purpose of biological research, medical investigations (for screening normal from pathologic tissues, for example), forensic or biotechnology applications.

The expression "non-linear optical response" designates the photons, hereafter called "response photons", which are emitted by chromophores, naturally contained in a sample, when they are excited by several (at least two) synchronized photons. More precisely, the expression "non-linear" means that the efficiency for the excitation of molecules varies in a non linear way with the electromagnetic field amplitude. In fact, the efficiency of the excitation by n synchronized photons is proportional to the nth power of the amplitude, while the efficiency of the excitation by a single photon (linear response) is simply proportional to the amplitude.

BACKGROUND OF THE INVENTION

As it is known by the person skilled in the art, the optical imaging of biological samples can be achieved through a large number of methods that can be classified, for the sake of simplicity, in three classes according to the physical mechanisms by which optical contrast is obtained.

The first class refers to methods based on spatial variations of the light transport properties. The classical methods are mainly based on contrast of absorption, reflectivity, refringence, birefringence, or polarization. Whatever the light transport property, it does not yield direct information about the sample biochemistry.

The second class refers to methods based on contrasts produced by "extrinsic" signals resulting from the optical excitation of well defined extrinsic luminescent molecules, introduced in the sample and selected both for giving strong optical signals and specific molecular recognition properties. The use of extrinsic luminescent contrast agents is time-consuming and requires constraining labelling procedures.

The third class refers to methods based on contrasts produced by "intrinsic" signals resulting from the optical excitation of well defined intrinsic molecules naturally present in the sample. Classically these methods offer lateral and depth resolutions which are insufficient for revealing the intimate tissue structures at cellular and subcellular scales.

The methods of the second and third classes may be based on the linear or non-linear optical response. But, as explained hereafter, it is preferable to use the non-linear optical response.

Indeed, when imaging intrinsic or extrinsic signals deep into a sample that is thicker than the depth of focus, the light must be directed toward the focus plane, and contrast information must be directed backwards or forward to the detector. So, an optimal light transport would require that the sample be transparent for excitation and emission light, and an optimal contrast would require that the sample not be transparent to the molecular excitations.

It results from this paradox that i) linear imaging microscopy technique can hardly perform deep tissue imaging and ii) endoscopic fluorescence imaging cannot resolve signals coming from the surface from those produced by deep chromophores. In contrast, the non-linear imaging uses a long wavelength near-infrared laser light which is in the transparency spectral window of the biological sample. So, the excitation light minimally interacts with the tissue on its way to the focus, which means that the transparency/excitation paradox of linear imaging techniques is solved, at least within a useful light penetration boundary which is currently at around 0.5 mm with excitation wavelength in the 700–1100 nm range. But, as in the case of linear fluorescence microscopy, intrinsic signals are considered as background noise and filtered out with appropriate optical filters.

Methods have also been proposed for extracting information about the metabolic status of a biological sample, in vivo or ex vivo, or for resolving histopathological features, like the malignancies of tumors, using intrinsic fluorescence or Raman emission spectra and lifetime. But, these so-called "spectral pathology" methods have been implemented with a linear excitation, thus leading to three major disadvantages:

i) since excitation is not confined at a focus, the linear spectroscopy is not spatially resolved and intrinsically bears strong limitations in terms of lateral and depth resolutions, as well as deep imaging.

ii) "Single-photon" fluorescence excitation spectra most often display a single and narrow peak, and one laser wavelength will only excite few molecular components. This puts stringent conditions on the choice of excitation wavelengths, and often leads to complicated spectroscopic criteria for resolving pathologic situations from healthy ones. This is for instance the case of intrinsic imaging of skin lesions or single point intrinsic fluorescence spectroscopy of the colon, where several wavelengths are necessary for one discrimination.

iii) Since spectral anomalies are produced by molecular sources which are not uniformly distributed in the sample, but most likely concentrated in specific cell types or subcellular structures, their spectroscopic contribution might be locally dominant in the wavelength and lifetime domain. Nevertheless, these local contributions are never dominant features in the final spectrum and therefore are difficult to extract, because they are spatially averaged out.

To summarize, every spectral diagnostic method implemented with linear excitation results in a very poor spatial resolution, a frequent need for multiple sources, a limited sensitivity, and an impossibility to get information at the cellular scale.

SUMMARY OF THE INVENTION

An object of the invention is to provide a solution to at least part of the drawbacks described above, and more particularly to make it possible i) to get images showing the geometric structure of a biological sample with resolution ranging from the sub-micron scale (cellular and sub-cellular scales) to the scale of tissular and organ structures, from a non-linear intrinsic imaging (microscopy, macroscopy or endoscopy), and ii) to combine such non-linear intrinsic imaging with spectroscopy for tissue exploration and diagnosis (or more generally detection of differences between normal and abnormal tissues).

To this end, the invention provides means appropriate to acquire images of the intrinsic non-linear optical response which may be resolved spatially in two dimensions (2D, or XY) or three dimensions (3D or XYZ), and, additionally, spectrally in lifetime (τ) and/or wavelength (λ).

More precisely, the invention provides an installation for multidimensional laser scanning of a material comprising intrinsic chromophores responsive to excitation by photons of at least one chosen energy to produce response photons. This installation is characterized by:

at least one source capable of producing time stamp pulses of synchronized photons, means for locally focusing the pulses on a material to investigate, to cause its intrinsic chromophores to absorb groups of at least two synchronized photons to produce non-linear response photons, means for directing the response photons to at least one collecting zone, means for collecting the response photons in the collecting zone(s), whatever their energy, processing means for converting the collected photons into data at least representative of their number, and storing the data in correspondence with at least the time stamp pulses that cause the material to produce the response photons, means for scanning the pulses through a chosen area of the material, and means for delivering from the data stored an image representative of the material chosen area, with a sub-millimeter resolution, and as a function of the respective time stamp pulses of the data.

Thanks to this spectroscopic integral, the response photons emitted by intrinsic chromophores of numerous components of the material are collected, whatever their radiative de-excitation channel (fluorescence, luminescence, non linear Raman and non linear Rayleigh (generation of second and third optical harmonics)). Therefore, the installation is able to deliver images with a high resolution extending from the cellular scale to the sub-cellular scale.

The Rayleigh and Raman processes do not involve photon absorption stricto sensu, but in the present specification absorption will still be used for simplicity.

Preferably, the collecting means comprises detector means capable of discriminating the response photons as a function of their respective arrival time and/or their respective energy (or wavelength), and the processing means is configured for storing the data in correspondence with at least a time stamp pulses and an arrival time and/or energy (or wavelength). Thus, it is possible to extract from the stored data only a part representative of a chosen region of the (λ,τ) plan in order to determine their originating molecular component(s).

In preferred embodiments, the collecting means and directing means are parts of a microscope, a macroscope or an endoscope.

The apparatus may include other characteristics taken separately or in combination, as defined in claims 2 to 35.

The invention also provides a method for multi-dimensional laser scanning of a material comprising intrinsic chromophores responsive to excitation by photons of at least one chosen energy to produce response photons. This method is characterized by the following steps:

producing time stamp pulses of synchronized photons, locally focusing the pulses on a material to cause its intrinsic chromophores to absorb groups of at least two synchronized photons to produce non-linear response photons, directing the response photons to at least one collecting zone, collecting the response photons in the collecting zone(s), whatever their energy, converting the collected photons into data at least representative of their number, and storing the data in correspondence with at least the time stamp pulses that causes the material to produce the response photons, scanning the pulses through a chosen area of the material, and delivering from the data stored an image representative of then material chosen area, with a sub-millimeter resolution, and as a function of the respective time stamp pulses of the data.

The method may include other characteristics taken separately or in combination, and in particular the collected photons may be converted into data representative of their respective arrival time and/or energy, and stored in correspondence with at least a time stamp pulses and an arrival time and/or energy.

BRIEF DESCRIPTION OF THE DRAWINGS

Other characteristics and advantages of the invention will appear on examining the following detailed description and the accompanying drawings, in which.

The accompanying drawings are essentially certain in character. Consequently, they can serve not only to complement the invention, but also to contribute in defining it, where appropriate.

DETAILED DESCRIPTION OF THE PREFERRED EMBODIMENTS

In the description below, reference is made to an installation and a method for multi-photon imaging of a biological material. More precisely, reference is made, purely by way of example, to a multi-photon imaging microscope.

As mentioned above, the invention refers to an installation (or instrument) that permits laser scanning imaging of a biological sample chosen area, in an appreciably continuous way or at selected discrete points, in two (2D) or three (3D) dimensions, by moving either a laser beam or the sample holding stage, or both.

At each scanning point, with a dwell time between two successive points typically ranging from 100 microseconds up to seconds, a light emitted by a pulsed laser source is focused in a "focal volume" within or at the surface of the sample. The intrinsic chromophores comprised in the sample absorb groups of at least two synchronized photons to produce non-linear response photons which can be collected and integrated on several kinds of detectors: (1) a point detector such as a photo-multiplier tube (PMT) or a semi-conductor based detector (or more generally a 2D imaging detector), (2) a 2D semiconductor array detector, coming after a dispersing element, for resolving the wavelength composition in one direction along with a spatial resolution in a perpendicular direction, (3) a set of a discrete point detectors in parallel, coming after optional chromatic filters and arranged to provide lifetime information, (4) a streak camera for 2D spectroscopic resolution in the wavelength/lifetime plane ($\lambda,\tau$), coming after a dispersing element.

Figure 1:
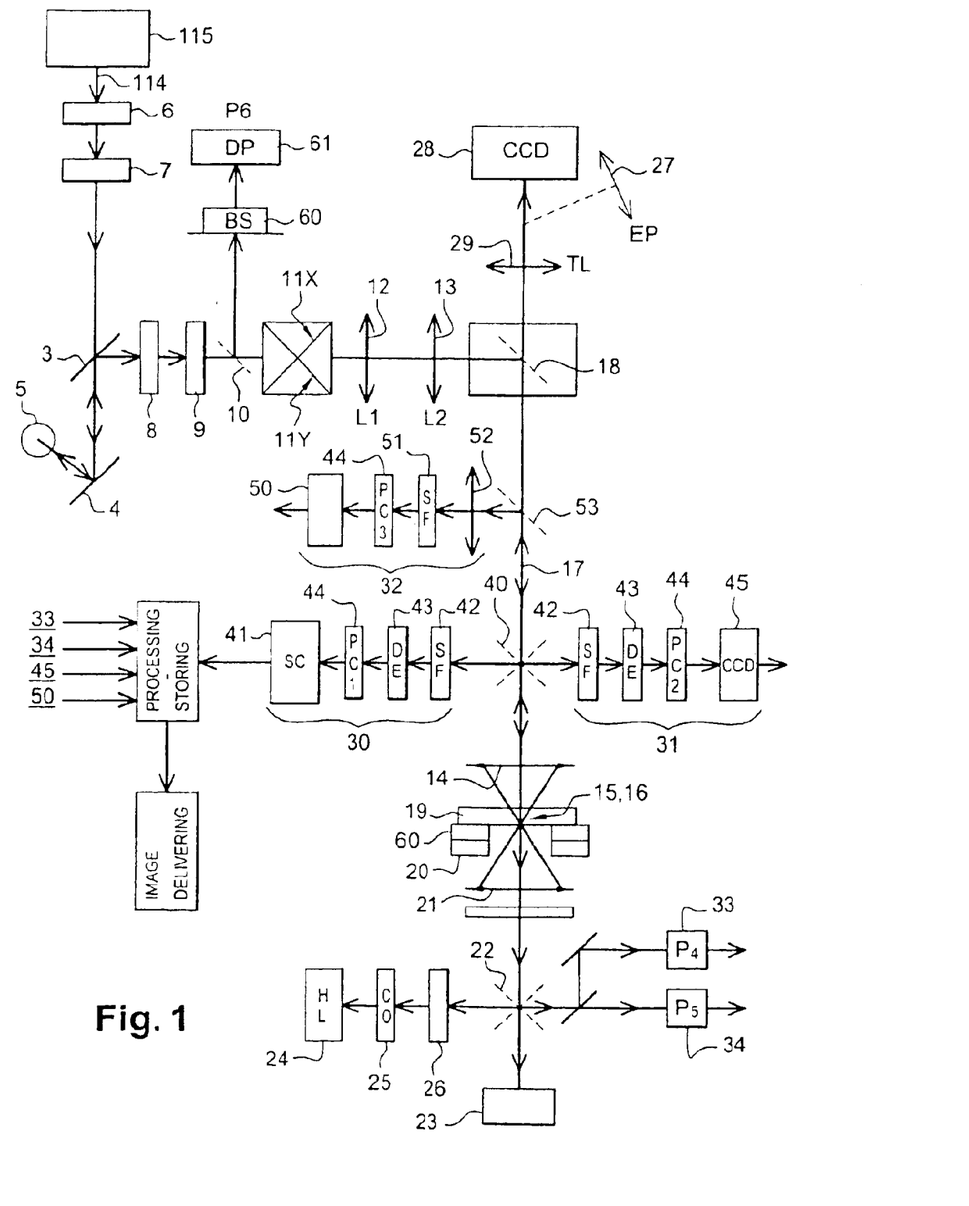
FIG. 1 is a diagram illustrating an apparatus of the invention.

The embodiment illustrated in FIG. 1 contains several optical ports for simultaneously using different combinations of the 4 above mentioned types of detection, or rapidly switching from one single detection mode to another one. In the following description, a "5D imaging" refers to the combination of a 2D spectroscopic resolution of the sample response in the plane ($\lambda,\tau$) with a spatial resolution provided by a 3D laser scanning (XYZ); and a "4D imaging" refers to the combination of a 2D spectroscopic resolution of the sample response in the plane ($\lambda,\tau$) with a spatial resolution provided by a 2D laser scanning (XY), or to the combination of a 1D spectroscopic resolution of the sample response in $\lambda$ or $\tau$ with a spatial resolution provided by a 3D laser scanning (XYZ).

Since biological samples can either be accessed from only one side, like bulk tissues, or from both sides in the case of thin enough sections, the preferred embodiment is based on a configuration in which i) the laser beam and associated scanning optics comes from one side of the bulk sample, e.g., from the top if an upright configuration is used, and ii) a sample holder for receiving the opposite side of the bulk sample without any optics, or equipped for two exclusive optical functions, namely trans-illumination or detection. The setup incorporates the possibility of direct optical control in trans-illumination mode, using either visual inspection through eyepieces or a simple imaging device like a Coupled Charge Device (CCD).

Another basic principle of the proposed configuration is that detection ports are built to bring detectors as close as possible to the light collecting optics, so as to minimize optical losses and the effects of geometric dispersion.

Figure 3:
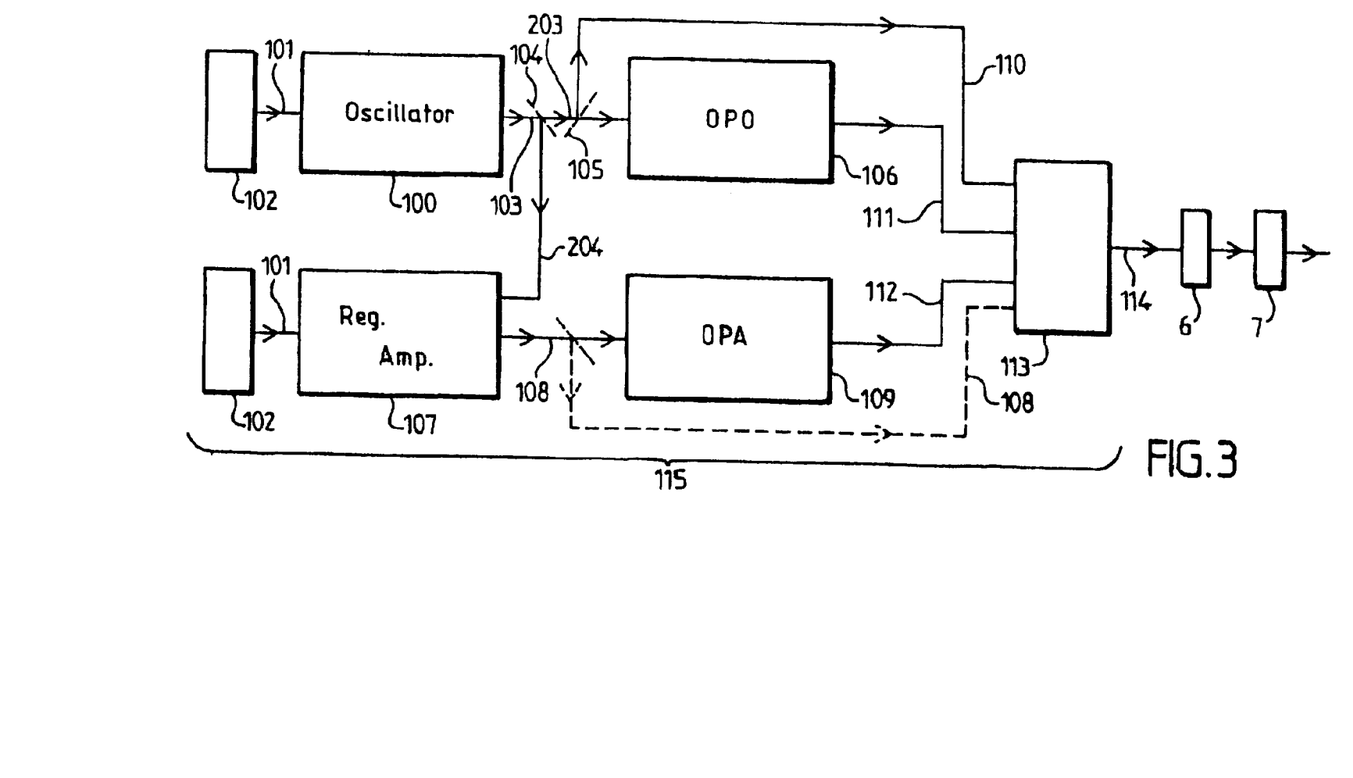
FIG. 3 is a diagram illustrating a laser source setup for the installation of FIG. 1.

In FIG. 1 an excitation light 114 is produced by one of several possible lasers of a laser source setup 115, producing ultrashort time stamp pulses of different wavelengths, peak energies, pulse duration and repetition rates, respectively and preferably. An example of laser source setup 115 is illustrated in FIG. 3. The laser power is controlled by a set 6 of one or two electro-optical modulators for two distinct purposes: the first modulator is used as a manual or low frequency computer-controlled intensity shutter possibly coupled to the scanning timing control, while the other modulator is used as a resonant high frequency modulator either for synchronous detection or for suppressing pulses for reduced repetition rate.

Notch filters 7 for Raman imaging can be installed downstream the electro-modulator(s) 6. Further, a system 3, 4, 5 for precompensation of temporal dispersion is preferably installed by either a set of two antiparallel prisms or gratings 5, with a flat input coupling mirror 4 and a flat output coupling mirror 3. The laser output polarization is then controlled by an optional element 8, which can be a $\lambda/2$ or $\lambda/4$ plate. Beam shaping is optionally achieved if necessary with a simple 2-elements telescope 9 designed with one divergent and one convergent lenses to avoid beam focalisation.

The laser beam then traverses an optional dichroic mirror 10, towards a set of two coupled galvanometric mirrors 11X and 11Y for point scanning in the X and Y direction, which steers the beam onto a set of two converging lenses 12 and 13. Via an optional flat mirror 18, the two lenses 12 and 13 conjugate the plane of the galvanometric mirror 11X or 11Y with the back aperture of the lens 14 that focuses the excitation light at a current focus 15 within the sample 19. The current focus can either be axial at position 16, i.e., on the optical axis of the lenses 12, 13 and 14, or away from the axis depending on the position of the galvanometric mirrors.

The excitation beam 17, between 13 and 14, is collimated, and the response photons emitted by the intrinsic chromophores of the sample are therefore also approximately collimated, which simplifies the optical design. In addition, the free space between 13 and 14 is large enough for implementing detection ports 30, 31 and 32 for a better detection efficiency. The lens 14 can either be a true single lens, an achromat, or a compound set of lenses like a microscope objective. The lens 14 can also be replaced with a purely reflective objective. This is particularly important when a spectral imaging involves UV emission, or requires optimal IR transmission, or minimal chromatic dispersion or else requires minimal temporal dispersion of the light exciting the sample or emitted by it.

The sample 19 can either be a thick one with observation limited to one side, or a thin sample with possible optical access from both sides. The former case is treated as a truncation of the setup shown in FIG. 1, by which the sample holder and all optical elements below it are replaced with a sample holder only, of the same type, or possibly more bulky for heavier samples or materials. In FIG. 1, it is focus on the case of the two-sided access. The sample 19 is mounted on a plate 60 (or sample holder) which is fixed to an XYZ translation stage 20 moved by mechanical motors or piezoactuators, or else a combined mechanism. The lenses 14 and 21 can also be moved along their axis. The light emitted by the current sample focus 15 is collected by both lenses 21 and 14.

By inserting a large flat or curved dichroic 21 below, the response photons (or sample light) can be reflected backwards it and toward the detection ports 30, 31 and 32, while excitation light is being transmitted forward to the dump.

The lens 14, is confocal with lens 21, and similarly to the former, can be replaced with any of the following elements: a true single lens, an achromat, a compound set of lenses like a microscope objective, or a purely reflective objective. Unlike lens 14, lens 21 can also be replaced with a non dispersive element like a purely reflective condenser. The optical conjugation of the two lenses 14 and 21 is better but not necessary, since downstream detectors (or detection ports) P4 and P5 are set close to the back aperture of lens 21. In particular, to keep these two lenses 14 and 21 at the optimal location, the Z-motion must be preferably achieved by the sample holder 60.

The light collected by the below lens 21 can be directed toward two detection ports 33 and 34 named P4 and P5, through a dichroic mirror 22. This dichroic mirror 22 is used for separating the light (response photons) emitted by the sample, which is in the visible or UV range, from the excitation light which is in the near infrared (NIR) or infrared (IR) range. The latter excitation beam light is sent through the dichroic mirror 22 toward a beam dump 23. Conversely, sample light (or response photons) can be directed back to the sample for further epicollection by inserting a flat or curved mirror between 21 and 22. The same dichroic 22 is also used for directing toward the sample a visible light coming from a halogen lamp 24, trough the appropriate condensing optics 25 and hot filter 26. This visible light is used for trans-illumination of the sample. The corresponding image is sent toward eye-pieces 27 for direct visualization or a CCD 28, through a tube lens 29. In that case of course, the mirror 18 is removed.

By replacing the mirror 18 with a dichroic mirror, one can also directly image, on the CCD 28, the light (or response photons or sample signals) emitted by the sample upon excitation by the laser beam 17. Finally, the sample signals resulting from the excitation laser beam 17 can be detected on detection ports 30, 31 and 32. This involves one dichroic mirror 40 that can be translated into the optical path and rotated along the optical axis of lens 14 to direct the light in opposed directions toward 30 or 31. These two opposed and exclusive collection ports 31 and 32 can be equipped for spectroscopic imaging, but their use is exclusive.

A third detection port 32 can be used simultaneously with either port 30 or 31, and is preferably a compact size point detector 50, like a PMT or a semiconductor-based detector. This point detector 50 is coupled to a port connector in front of a shutter/filter assembly 51, and preceded by a lens 52 that conjugates the detector input plane with the back aperture of the lens 14, to provide a Fourier imaging of the sample signals. A sliding dichroic filter 53 directs the sample signals toward lens 52. The detector 50 can also be located at the detection port 33 (P4) or 34 (P5)

One of the two detection ports 30 and 31, for example 30, is preferably equipped with a streak camera 41, in front of which are installed a shutter and filter assembly 42, an element 43 for chromatic dispersion and focalisation (or dispersing element) onto the streak camera 41 photocathode window, and a coupling mechanism 44 for adjusting the position of the streak camera 41 relative to element 43. Details on the streak camera 41 and its coupling are given below with reference to FIG. 2. The other port 31 can be equipped with a spectral imaging detector described below in the 4D spectral imaging section. There is no reason for using these two types of detections simultaneously. Noteworthy, any of the two detection means 41 and 45 can also be located beyond the sample at the location of the detection port 34.

At last, a detection port 61 (or P6) with a beam streering 60 is preferably available upstream the galvanometric mirrors 11, at a position which is de-scanned (i.e., the beam of response photons is approximately fixed in position). At that position, any detection means mentioned above can be used while scanning.

The streak camera 41 is aimed at analyzing sample signals in the ($\lambda,\tau$) plane, which means that the excitation beam 17 must be fixed, and preferably axial. Imaging is then achieved by a 2D or 3D sample motion with a motor and/or piezo-actuators. Such a streak camera 41 can be coupled to any of the three exit ports 30, 31 or 35.

Figure 2:
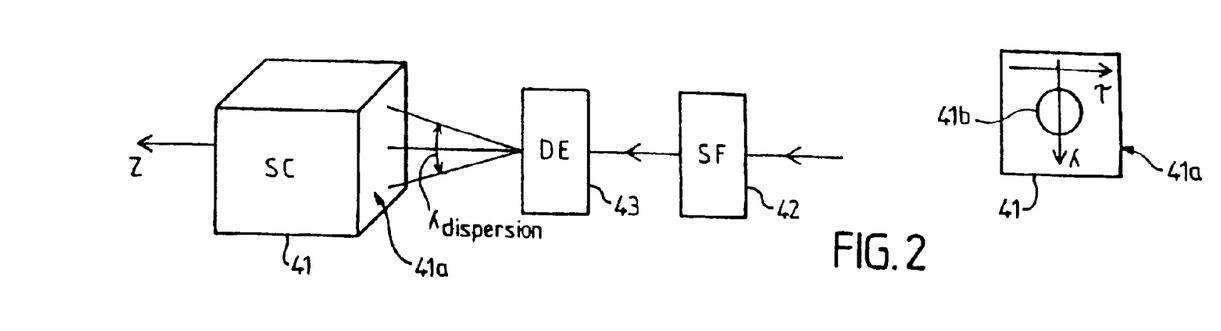
FIG. 2 is a diagram illustrating the input window of a streak camera, for the installation of FIG. 1.

The response photons (light) emitted by the sample are reflected by the dichroic mirror 40 or 22 and go first through a "shutter/modular filter" assembly 42, for protecting the streak camera 41, and for installing any sort of chromatic or neutral density filter required for analyzing the non-linear optical response of the sample as whole or in part. The response photons are then dispersed by a prism assembly or a grating 43 (or DE) before being focused by a lens or the grating 43 itself onto the streak camera input window 41b located on its input face 41a (as illustrated in FIG. 2), which then resolves the photons in time in the perpendicular direction. The streak camera 41 works in a synchroscan mode in phase with the laser frequency, or at a submultiple of that frequency using a pulse selection device. The selection of the center wavelength and the dispersion gain to be analyzed on the streak is achieved by translations of the dispersion coupler 43.

In a different configuration, the dispersing element 43 can be removed so that one direction of the streak camera 41 be used for lifetime ($\tau$) imaging, and the perpendicular direction of the streak camera 41 be used in conjunction with line scanning for imaging lifetime along lines in the sample. In that case the scanning strategy is very similar to that described below for 4D (or 5D) spectral imaging, the difference lying in the fact that the time deflection direction of the streak camera 41 corresponds to the spectral dispersion direction of the 4D (or 5D) detection system.

Reference is now made to FIG. 3 to describe an example of a laser source setup adapted to non-linear imaging installation according to the present invention.

A multi-photon excitation able to induce a non-linear optical response (for example fluorescence response photons) requires a high instantaneous power which can be achieved by different types of lasers providing very short pulses in the visible red or near infra-red region. Mode-locked lasers providing 60–100 fs (femtosecond) pulses with wavelengths in the 700–1050 nm range are typical sources for multi-photon excitation imaging. Picosecond sources can also be used. Because the present invention aims at exciting the intrinsic non-linear response of tissues in a very general way, including not only fluorescence but as also luminescence and non-linear Raman and Rayleigh responses, a wider range of short pulsed sources must be preferably used. Several parameters may be used for choosing such a laser source: the wavelength, the pulse duration, and the pulse energy and repetition rate.

Wavelengths, classically selected in the 700–1050 nm range, cannot be chosen much deeper into the visible range since linear excitation of tissues will arise and advantages of non-linear excitation will be lost. To the contrary, higher wavelengths in the limit of water transmission are advantageous for several reasons: (i) it allows a reduced scattering from tissues, (ii) it might allow an improved tradeoff between low absorption and low scattering, (iii) it allows a reduced temporal dispersion in optical elements and optical fibers. Noteworthy, wavelengths in the 1–1.6 $\mu$m (micron) range provide non-linear sub-resonnant excitation of intrinsic chromophores, and is therefore more selective for non-linear Raman and Rayleigh excitation with respect to unwanted fluorescence excitation. Raman can also be excited in the present method in the UV resonant mode, via a non-linear excitation of the 700–800 nm fundamental radiation, preferably in the picosecond mode. To this end a 3 synchronized photon excitation is preferable, especially for DNA detection. In particular second or third harmonics (non-linear Rayleigh), or three photon imaging of intrinsic tissue components is easier with a wider range of excitation wavelengths.

The pulse energy is an important concern for biological imaging since the depth penetration is limited by the power at the sample focus. As known by the person skilled in the art, the penetration depth in a given sample is approximately scaling as the logarithm of the laser power. For example, the classical mode-locked oscillators for laser source, actually used for non-linear fluorescence, provides pulses in the 1–10 nJ (nanojoule) range, which leads to an approximate effective microscopic imaging depth of 0.5 mm in in situ and ex situ tissues. Higher energy pulses can give access to deeper regions, but it can induce tissue damage, not necessary at the sample focus, but already at the surface of the sample. Nevertheless, amplified parametric oscillators (OPA) giving pulses in the microjoule ($\mu J$) range can be used for tissue imaging, with an appropriate optics for focusing the laser beam into the sample (for example a special optical design with large surface lenses, or large catadioptric devices), as described hereafter.

Advantageously, the installation of the present invention uses one of several pulsed lasers, which are selected only for the beam characteristics they produce: pulse duration, energy, wavelength. The very nature of the crystals employed in the laser sources is not of central importance, other laser designs could be used as long as they produce similar radiations. In order to image nonlinear intrinsic optical responses in the most flexible way, the preferred embodiment comprises a set of laser sources illustrated in FIG. 3. Of course, not all of these lasers are simultaneously required, and any subset of these laser elements is enough for the invention, as long as it produce a useful radiation.

The whole laser source setup that will be described hereafter, as an example, corresponds to the element 115 in FIG. 1.

A Ti:Sapphire oscillator 100 is pumped by a continuous laser beam 101 at 532 nm, produced by a 5/10 W solid-state laser 102 (other oscillators, and especially crystal oscillators, may be used). This first oscillator 100, produces a femtosecond (for example 60–100 fs) or picosecond (for example 1–4 ps) pulsed beam 103 in the 700–1050 range, with an average power up to 1.8 W and a repetition frequency of 76–80 MHz. The beam 103 impinges on an optional flat semi-reflecting mirror 104 which directs a part 204 of this beam toward a regenerative amplifier laser cavity 107. The remaining part 203 of beam 103 is optionally reflected, totally or partially, by a flat mirror 105 as a beam 110 toward a beam selector 113. The remaining part 203 can, partially or totally, enter into an optical parametric oscillator 106 which produces femtosecond or picosecond pulses 111 preferably with temporal characteristics similar to beam 110, with a slightly reduced pulse energy but wavelengths in the 1–2.4 $\mu m$ range. The regenerative amplifier laser cavity 107, when pumped by another laser identical to laser 102 and injected with beam 204, outputs microjoule-femtosecond (typically 130 fs) pulses 108 at a wavelenght of 800 nm and a repetition rate of 250 kHz. The pulses 108 are then converted within an optical parametric amplifier 109 into pulses 112, similar in duration, but not in repetition rate, to pulses 111, but in the 1.1–3.2 $\mu m$ wavelength region. It is also possible to directly use the beam 108 with the help of a (semi)reflective mirror.

Finally, beams (pulses) 110, 111, and 112 (and eventually 108) all arrive in a beam selector 113, that selectively outputs one of the input beams, or a combination of at least two of them. Since the laser cavity 107 only requires a very minor fraction of beam 103 to operate, and since the optical parametric oscillator 106 only needs 20 to 30% of beam 103 to operate, all three beams 110, 111, and 112 can be produced and used simultaneously. Again, the maximal flexibility of the present set-up is not absolutely necessary for getting satisfactory results with the present invention, and several possible subsets are sufficient for most applications.

Femtosecond and picosecond operation can in principle both be used for intrinsic imaging, but with distinct advantages in terms of excitation efficiency. In particular, picosecond mode as compared to femtosecond mode shows a more narrow spectrum which is required for resolving Raman lines, and is also better for propagation into optical fibers of considerable interest especially for endoscopic applications. In the picosecond mode, the notch filters are not necessary. As above mentioned the excitation beam can be modulated by an electro-optical modulator 6, either in a resonant way for pulse selection or at low frequency to serve as a shutter.

All lenses of the installation are carefully selected for their transmittance and antireflecting coating in the spectral range required by the application. The correction of chromatic aberration is not an important concern in selecting the focusing of optics. The correction of spherical aberrations is more important. In addition, imaging tissue often require low magnification objectives which have also a very low numerical aperture in general. For these reasons, it is preferable to use specific lenses having a large back pupil, a high numerical aperture, and a very good correction of spherical aberrations. Large pupils and beam expansion are necessary when the excitation beam comes from the OPA laser source 109 with microjoule pulses, in order to reduce excessive light power through the focusing element, but also to minimize the flux traversing the tissue surface. It is also important to select the optical elements while taking into account the fact that excessive temporal and spatial dispersion of refractive optical elements deteriorates the quality of spectroscopic analyses and the overall efficiency of the methods. Therefore, purely reflective elements are preferred as soon as it is possible, especially for lenses 14 and 21.

The above embodiment applies essentially to samples that can be brought onto a microscope or macroscope stage 60, 20 which can be translated but remains attached to a bulk installation. This includes classical isolated micro or macroscopy samples, but also more bulky samples that remain intact in their anatomic context, like a part (at least) of a human or animal body. But the invention also applies to another embodiment with a remote imaging head connected in a flexible way to the laser source.

Figure 4:
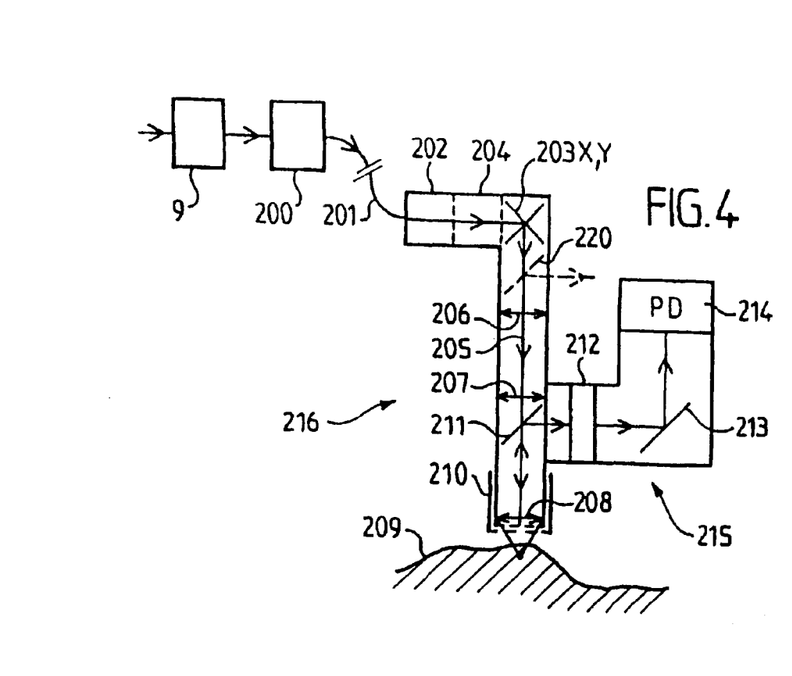
FIG. 4 is a diagram illustrating a first movable photodetector assembly adapted to non invasive micro or macroscopy.

One example of such an embodiment is illustrated in FIG. 4. An input coupler 200 is installed immediately downstream the beam shaping optics 9 and replaces the galvanometric mirrors 11X-Y of the installation of FIG. 1. This input coupler 200 focuses the excitation laser beam coming from the source setup 115 and establishes the proper position of a flexible light guide 201 in order to optimize the laser input. The light guide 201 can be, for instance, an optical fiber. The temporal dispersion inside the fiber 201 is preferably compensated by a proper adjustment of the pre-compensation elements 3, 4 and 5. The output of the light guide 201 is coupled to an output coupler 202 similar to the input coupler 200 and which produces a parallel beam that impinges on two galvanometric mirrors 203X and 203Y. These mirrors 203 steer the excitation light beam 205 through two lenses 206 and 207 toward a focusing lens 208, to image the galvanometric mirrors onto the back aperture of 208, in a way similar to the one described in reference to FIG. 1. The lens 208 focuses the excitation light beam 205 into the sample 209, at a relative distance from the lens that is adjusted by an adjustable sleeve 210.

The response photons coming back from the sample are then directed through a dichroic mirrror 211 toward a detection unit 215 comprising at least a filter 212, an element 213 that directs the photons onto a photodetector 214 (PD). In the most simple embodiment, the element 213 is a flat mirror, while the photodetector 214 is a compact photomultiplier tube (PMT); in that case an additional lens is preferably introduced for conjugating the back aperture of the lens 208 with the detector entrance. The element 213 can also be a small dispersing element (DE), the detector 214 then being a 2D array detector (for example a CCD) assembled for (λ,X) imaging, with one direction used for chromatic analysis of the signal, and a perpendicular direction used for sample scanning on the mirror. In that mode, lines are preferably scanned and analyzed at the frame frequency of the CCD detector. Small amplitude scanning in the Y direction, i.e., in the λ direction can be achieved without losing the spectral information, since successive Y-positions correspond to successive images, with a spectral offset that can be compensated for as a function of the Y-direction.

Figure 5:
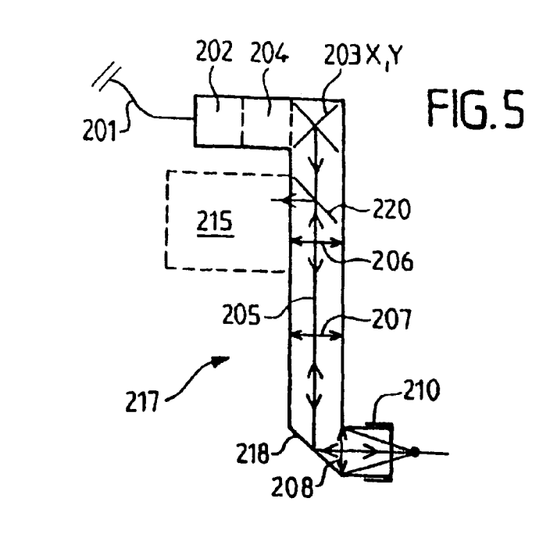
FIG. 5 is a diagram illustrating a second movable photodetector assembly adapted to non invasive micro or macroscopy.

In a variant, the element 213 can be a gated photomultiplier for time-resolved analysis. All the parts of the assembly connected to and downstream the fiber coupler are enclosed in a closed rigid mount 204. The photodetector assembly 215 can collect the response photons from a dichroic 211 positioned between lenses 207 and 208, or between the galvanometric mirrors 203 and the lens 220 as illustrated in FIG. 5, depending on the desired collection efficiency and/or accessibility. In the latter case, shown in FIG. 5, one can use the detectors above mentioned in reference to FIG. 4. Moreover a lateral observation of the material is also possible at a right angle with a mirror 218.

Figure 6:
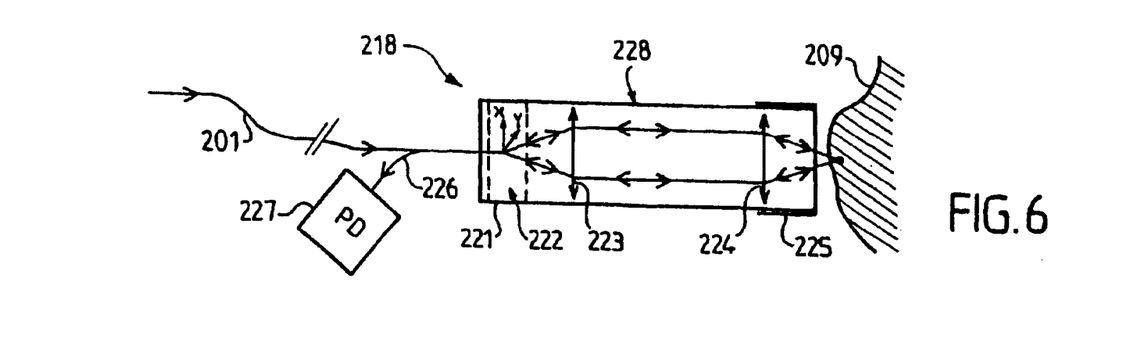
FIG. 6 is a diagram illustrating a photodetector assembly adapted to endoscopy.

Another alternative embodiment is illustrated in FIG. 6. This embodiment is more particularly adapted to non-linear intrinsic imaging in an endoscopic mode. In that case, the fiber ouput coupler 221 includes a remote control device 222 which can move the tip of the fiber in two perpendicular directions in the focal plane of a coupler lens 223. The excitation light emerging from the core of the fiber tip is directed by lens 223 to a focusing lens 224 in order to be focused into the sample 209 and scanned correspondingly in the focus plane. To this end, the lens 224 is in the focal plane of the lens 223. Again, a sleeve mechanism 225 positions the focus plane inside the sample. Parts 222–225 of assembly 218 are enclosed in a small diameter and rigid tube 228. The response photons emerging from the sample 209 are preferably collected by a large cladding around the fiber core, and then split away from fiber 201 into a collecting fiber 226 that directs them toward a photodector assembly 227 similar to the assemblies referenced 215.

The non-linear imaging of a sample 19 comprised at least the steps mentioned hereafter.

In a first step one produces time stamp pulses of synchronized photons of at least one chosen wavelength, with the source 115.

In a second step the pulses are locally focused on a first part of a chosen area of the material (sample) to cause its intrinsic chromophores to absorb groups of at least two synchronized photons and de-excite themselves by emitting photons of energies depending from their respective constitution (more precisely their specific energy transitions) and from the multiphotons excitation wavelength.

In a third step, the photons emitted by the sample (response photons) are directed to at least one collecting zone located at 50 or 33 or 34.

In a fourth step, the response photons are detected, whatever their energy, by a detector, for example a point detector, with a high sensitivity over the widest possible region of the spectrum, ranging from the UV region to the near infra-red (NIR) region, for example around 800 nm. In contrast to all the non-linear imaging installations known in the art, the only filter of the installation is the one used for rejecting the excitation light. So, one carries out a spectroscopic integration, of all the largest accessible region of the (λ,τ) plane, resulting from the intrinsic chromophore emission produced by all possible photo-physical mechanisms (radiative de-excitation channels), like for instance, fluorescence emission, Raman and Rayleigh scattering.

This step is aimed at 2D or 3D spatial sample imaging using its intrinsic non-linear optical response as completely as possible.

In a fifth step, the detector converts the collected photons first in an analog physical signal, for example a voltage or a current, and then in data at least representative of their number. The data are then stored in correspondence with at least the time stamp pulses that cause the intrinsic chromophores to produce the response photons. Of course, when the detector is able to discriminate the different wavelengths λ and/or arrival time (or lifetime) τ, the data are also stored in correspondence with the wavelength and/or arrival time.

Then in a sixth step, one carries out again the second to fourth steps for every other parts of the material area. This is achieved by scanning the pulses through the area. It can be a 2D or 3D spatial scanning.

Finally, in a seven step, one delivers from the stored data a full image representative of the material chosen area, with a sub-millimeter resolution, and in function of their respective time stamp pulses.

Other examples of imaging methods will now be described. According to the first method, one first records a 2D or 3D image of the sample as above described, by capturing the full response (or spectroscopic integral), referring to the signal integration in the (λ,τ) plane. This full response image, most simply IC captured by a point detector located at 50, 33 or 34, such as a photomultiplier or an APD. A more complete spectroscopic response can possibly be established using at least one other excitation wavelength, so as to make the following step easier.

Then, the resulting image, which is in general quite contrasted, is processed to identify its main geometric components, through a possibly automatic image segmentation procedure, from which the size, the volume, the respective intensity of the components are assessed. In some cases, this simple analysis, only based on the spectroscopic intregral and devoided of any spectroscopic analysis, is enough for the purpose of recognizing features, normal and abnormal, at the tissular, cellular, or subcellular level. In particular, proliferation centers can be seen, as well as geometric disorders of the cellular arrangement, and extracellular feature.

Alternatively, once the spectroscopic integral image has been segmented, a full spectroscopic analysis in the (λ,τ) plane is carried out for extracting specific spectroscopic signatures of the different regions of the material. This set of signatures can then either serve to construct a large database, with comparison to the known material region information, or be interpreted in terms of diagnosis by comparison with existing signatures stored in a database.

In a variant of this method one only acquires the λ-spectrum of the tissue response. This is simply accomplished by coupling a sensitive 2D CCD detector 45 in the optical port 31 of FIG. 1, behind a protective or selective shutter/filter assembly 42, and a dispersing/focusing element 43. Again, as for the streak camera 41, the dispersing element 43 (or DE) is mechanically installed in order any given wavelength region of interest can be easily selected. A 4D spectral imaging is achieved by driving one of the galvanometric mirror 11X along a line perpendicular to the wavelength dispersion element 43, and using a bi-directional (array) CCD chip 45 installed in such a way that one of its directions is that of the wavelength dispersion, while the other is that of the scanning mirror movement, for example X. The perpendicular direction Y of scanning of the laser beam relative to the sample can be executed either by the other galvanometric mirror 11Y or the sample holder 20,60. A full 2D scanning pattern can be achieved at a line frequency equal to the line frame frequency of the CCD 45, with slow perpendicular motion in direction Y or even Z.

The second method starts from the spectroscopic signatures established in the (λ,τ) plane or most classically in the λ domain, and obtained according to the first method. Here, a signature most generally designates a scalar function that transforms a given distribution of points in the (λ,τ) plane into a scalar, e.g., the weight of a region of interest or the ratio of two weights. Selected signatures are then used to image the entire sample, or part of the sample, and produce images in which the intensity is given by the selected signature(s). The relevance of the selected signature then reveals the localisation, the shape, and the extent of the targeted structure, which can be quantitatively assessed.

The third method does not assume any previous knowledge, nor the assumption that the spectroscopic integral can be used for segmentation purposes. In that case, the full 5D image (3D spatial and 2D spectral) is established, and information is sought after in the 5D space. Various methods are employed to reveal differentiated spectral and possibly geometric structures, e.g., entropy minimisation methods, principal component analysis or other linear algebra tools.

As above mentioned, in contrast to the non-linear images delivered by the installations of the art, the method and installation of the invention aim at imaging the total intrinsic response of a sample as completely as possible, produced by all the photophysical mechanisms, resonant or non-resonant, elastic or not-fluorescence. These images show a quite complete picture of tissue structures from the millimeter scale down to subcellular scales, with micron resolution. Therefore the invention allows the instantaneous visualization of tissues, cells and various subcellular organelles, without any labelling procedure.

Another major advantage of the invention is that the present non-linear spectroscopy carried out at successive points resolves local singularities of the spectrum that are spatially "diluted" out in the average spectrum. In contrast, these local singularities are locally dominant and thus much more easily detected. Consequently the present invention is more sensitive than bulk spectroscopic methods, and shows intrinsic structures much better and deeper than other imaging tools. In addition, the invention is useful for establishing a more rich and efficient set of spectral signatures, not only because they can be truly 2D (λ,τ), but also because they are correlated with the tissue geometry. Because these photophysical signatures can now be localized within the cell, between cells, and at the scale of tissular regions, it is more easy to interpret them in terms of their molecular origin. Therefore, interpretations of these spectroscopic signatures in terms of cellular biochemistry are now possible at the microscopic scale, with potentially very interesting insight into pathophysiological mechanisms such as cell proliferation control, intercellular interactions within tissues, cell shape, intracellular secretion mechanisms and ischemia.

The spectroscopic signatures based on intrinsic fluorescence Rayleigh and Raman excitation and in particular, but not exclusively, those established for various normal and pathologic processes in cells and tissues are accessible by the present non-linear excitation method and installation. Therefore, straightforward applications of the present invention are all applications in which intrinsic response of cells and tissues are probed by non-linear excitation to establish images either resolved in at least one spatial dimension and at least one spectroscopic dimension, or based on a full 2D spectroscopic integration (λ,τ).

A very large number of tissue components have been shown to yield an intrinsic fluorescence response upon single photon excitation, such as: tyrosine, porphyrins, flavins, NADH, NADPH, serotonine, dopamine, collagen, melanins, hemoglobin, fuscins, indolamine and elastin. Serotonine, for instance expressed by enterochromaffin cells, can be seen and used for tumor detection Raman spectra, obtained according to the present invention, can be used to identify molecules such as: cholesterol, collagen, elastin, lipids (for example cholesterol, DNA, β-carotene).

Moreover, hyper-Rayleigh spectra, i.e., second and/or third harmonic responses, obtained according to the present invention, can be used to identify collagen and DNA, for example. Noteworthy, harmonic signals are sensitive to, and thus indicators of, a local ordering at a microscopic scale, which reveals collagen organisation and polar polymeric structures in general.

The present intrinsic imaging concerns in situ and ex situ observation of biological samples of plant material, procaryotes, animals and human beings, or bio-synthetic samples such as reconstituted tissues or chimeric tissues, and more particularly wood, plant, animal or human cells, tissues or organs, artificial organs such as reconstituted skin, implanted xenogenic or autologous living or fixed tissue structures. Consequently, the invention applies to biological research, biotechnology (such as imaging of reconstituted tissues), forensic investigation applications and medicine. At least the following tissues can be imaged: skin, oral mucosa and submucosa, intra and extra ocular tissues concerned by ophthalmologic investigations, upper and lower respiratory tract, oesophagus, lungs, aesophagus, breast, coronary arteries, gastro-intestinal tract, genital tract including the uterine cervix and endometrium, bladder and anus. For most of these tissues, fluorescence and/or Raman spectra can be used for component identifications. So the present invention can be use to obtain these spectra.

For these targets and other tissues, laser scanning imaging can be performed along with the same principles as those described with reference to FIGS. 1, 4 and 5 in non invasive macroscopic and microscopic modes, or to FIG. 6 in an endoscopic mode, with corresponding objectives such as high numerical aperture macroscopic objectives, with lens-based objectives as well as purely reflective ones.

The present invention offers four main imaging modes all based on a purely geometric imaging resulting from an unfiltered non-linear optical response of the sample (spectroscopic integral), preferably associated with:

i) at least one spectral dimension (λ and/or τ) or a signature elaborated from the spectroscopic plane (λ,τ), ii) a localisation of a specific spectroscopic signature by scanning with or without constructing a spectral image, iii) non-linear optical response of at least one specific extrinsic chromophore. This last mode is of particular importance in the context of the precise localisation of specific chromophores which requires a so-called counter stain in the methods of the art. With the present method, since major elements (or components) of cells or tissues such as cell boundaries, nuclei, or tissular organisation can be visualized with an intrinsic signal, no counter stain is required. The tissular and cellular anatomy is directly visible, while imaging and spectroscopic analysis of extrinsic chromophores can be carried out simultaneously.

This possibility of visualizing extrinsic chromophores together with the anatomic context revealed by the intrinsic response can be applied to several types of applications. Firstly, extrinsic signals can arise from pathology-related living objects such as bacteria, viruses or parasites, or from inert particles such as asbestos. Secondly, the tissue reactions toward or the tissue alterations related to the presence of these various infectious agents or inert objects can also be assessed by the present invention. Thirdly, signals can also arise from the presence of exogeneous substance related to drug abuse, or of interest for forensic investigations.

The invention also concerns medical diagnosis of targets in situ for intrinsic non-linear imaging without requiring any physical biopsy. The invention relates therefore to the detection of disorders in the skin tissue, including but not limited to melanoma or nevi that can be inspected and spectroscopically analyzed with micron resolution, thus revealing cell morphology, tissular lesions, and micro-vascularisation. It also concerns diagnosis of the oral cavity, with a remote sensing head such as 217 (of FIG. 5), to detect early evidence of tumor and cancer, namely using non-linear protoporphyrin optical response. This technique can supplement or even replace classical tissue biopsy and pathological evaluation, and can also supplement or even replace existing spectroscopy techniques which require several (up to 11) different wavelengths.

Colposcopy and uterine cervix investigation are also other applications of the present invention using a device with remote sensing head such as 216 (FIG. 4). Indeed, dysplasia and pre-invasive and invasive cancer can be detected using at least intrinsic fluorescence of the cervix epithelium, chorion, and deeper layers. In the case of uterine cervix epithelium, in particular due to its glycogen content, Raman signal signatures may also be detected under picosecond excitation. The strong intrinsic response of the colonic epithelium yields images showing the tissue geometry at the single cell level. The present invention also applies to direct in situ macroscopic or microscopic imaging of surgically exposed tissues, such as the GI tract, muscles, and central nervous system, to provide the physician with very important information relating to the tissular and cellular structure and metabolism to monitor the surgical procedure.

Cells or tissue specimen can also be visualized and analyzed by nonlinear intrinsic spectral imaging according to the present invention, with at least one spatial dimension and one spectral dimension for immediate diagnosis (or detection), in addition to a histopathological or cytopathological analysis.

Besides diagnosis purposes, non-linear spectral imaging according to the present invention can also be used in parallel with a laser-based procedure such as photodynamic local treatment (PDT) or photoablation. Indeed, while detecting tissular architectures and their abnormalities, intrinsic laser scanning imaging can be applied to guide another laser action following the same optical path. Laser beams used for photoablation or photodynamic treatment can thus be accurately targeted with single cellular pointing accuracy. Alternatively, the imaging beam (laser excitation) itself can be used for non-linear photo induced destructive activity at a local scale. In addition, non-linear spectral imaging can also be used to monitor the effect of these two types of action, by revealing the intimate tissue structure at cellular or subcellular scales. Finally, the same diagnosis (or detection) methods described above can be easily translated into follow-up methods for long term monitoring treatment effects and recovery.

The invention also applies to investigations aimed at drug localization and metabolization, to answer pharmacological and pharmacodynamic issues. With the present invention, drugs of interest, provided they can be made visible by non-linear excitation, will be localized in space and time in vivo, in the anatomical context of the tissues, with microscopic resolution. This should be very useful for the in vivo evaluation of drug design and delivery problems, or in gene therapy (visualization of genetically engineered elements, localization of gene products, cell proliferation and tissue modification).

Medical applications of the present invention to animal investigations also provide a set of straightforwardly derived methods for the investigation of animal diseases and animal models of human diseases.

The invention is not limited to the embodiments of the installation and the implementation of the method as described above purely by way of example, but it covers any variant that could be envisaged by the person skilled in the art within the ambit of the following claims.

In particular, the invention has been described with reference to the installation illustrated in FIG. 1, which is a very full one. But, the installation may be much more simple provided it comprises at least one collecting means for collecting response photons in at least one collecting zone, whatever the photon energy. In other words, the installation may be provided with one, two, three, four, five or six different collecting means located in different, collecting zones, or even more if required.

What is claimed is:

1. An installation for multi-dimensional laser scanning of a material comprising intrinsic chromophores responsive to excitation by photons of at least one chosen energy to produce response photons, said installation comprising:

at least one source (115) for producing time stamp pulses of synchronized photons, means (12–14) for locally focusing said pulses on a material to cause said intrinsic chromophores of said material to absorb groups of at least two synchronized photons to produce response photons, means (22,40,53) for directing said response photons to at least one collecting zone, means (30–34) for collecting said response photons in said at least one collecting zone, whatever their energy, processing means for converting said collected photons into data at least representative of their number, and storing said data in correspondence with at least the time stamp pulses that cause said material to produce said response photons, means (11) for scanning said pulses through a chosen area of said material, means for delivering from said data stored an image representative of said chosen area of said material, with a sub-millimeter resolution, and as a function of their respective time stamp pulses.

2. Installation according to claim 1, wherein said collecting means comprises detector means (41), for discriminating said response photons as a function of their respective arrival time, and said processing means is configured for storing said data in correspondence with at least a time stamp pulses and an arrival time.

3. Installation according to claim 1 or 2, wherein said collecting means comprises detector means for discriminating said response photons as a function of their respective energy, and said processing means is configured for storing said data in correspondence with at least a time stamp pulses and an energy.

4. Installation according to claim 1, wherein said collecting means is able to collect response photons emitted by said material according to radiative channels chosen in a group comprising at least fluorescence, luminescence, non linear Raman and non linear Rayleigh.

5. Installation according to claim 1, wherein said collecting means is able to collect response photons with wavelengths comprised between approximately 250 nm and 1 μm.

6. Installation according to claim 1, wherein said collecting means comprises a detection means configured as a point detector.

7. Installation according to claim 1, wherein said collecting means comprises a detection means configured as a set of discrete point detectors in parallel.

8. Installation according to claim 1, wherein said collecting means comprises a detection means configured as a bi-dimensional imaging detector (45).

9. Installation according to claim 6, wherein said collecting means further comprises, upstream said detection means (50), a lens (52) for focusing said response photons on said detection means, followed by a shutter and filter assembly (51) and by a coupling mechanism (44) for adjusting the position of said detection means (50) relative to said lens (52).

10. Installation according to claim 1, wherein said collecting means comprises a detection means configured as a streak camera (41).

11. Installation according to claim 10, wherein said collecting means further comprises, upstream said detection means (41), a shutter and filter assembly (42) followed by an element (43) for chromatic dispersion and focalisation onto a photocathode window of said detection means (41), and by a coupling mechanism (44) for adjusting the position of said detection means (41) relative to said element (43).

12. Installation according to claim 1, wherein said scanning means comprises, between said source and said material, a set of two coupled galvanometric mirrors (11X, 11Y) for point scanning said material in two perpendicular directions (X,Y).

13. Installation according to claim 12, wherein said scanning means further comprises, downstream said set of coupled galvanometric mirrors (11X,11Y), a set of two converging lenses (12) and (13) adapted for conjugating a plane of said set (11X,11Y) with a back aperture of a lens (14) adapted for focusing said pulses at a chosen focus (15) within said material (19).

14. Installation according to claim 1, wherein said pulse source (115) comprises an oscillator (100) pumped by a continuous laser beam (101) produced by a laser (102) for producing first ultrashort pulses (103) of a first wavelength.

15. Installation according to claim 14, wherein said pulse source (115) further comprises an optical parametric oscillator (106) for producing second ultrashort pulses (111) with temporal characteristics similar to those of said first ultrashort pulses (110), a slightly reduced pulse energy compared to the one of said first ultrashort pulses (110), and a second wavelength different from said first wavelength.

16. Installation according to claim 15, wherein said pulse source (115) further comprises a regenerative amplifier laser cavity (107) comprising a first input for receiving a part (204) of said first ultrashort pulses (103) and a second input to be pumped by a laser (102), and an output for delivering pulses (108) of a third wavelength.

17. Installation according to claim 16, wherein said pulse source (115) further comprises an optical parametric amplifier (109) for delivering, from said third ultrashort pulses (108), pulses (112) of a fourth wavelength with temporal characteristics similar to those of said second ultrashort pulses (111).

18. Installation according to claim 17, wherein said pulse source (115) further comprises a beam selector means (113) comprising four inputs for receiving said first (110), second (111), third (108) and fourth (112) ultrashort pulses, and one output for selectively delivering at least one of these first, second, third and fourth ultrashort pulses.

19. Installation according to claim 1, wherein it comprises, downstream said pulse source (115), a source power control means (6).

20. Installation according to claim 19, wherein said source power control means (6) comprises at least one electra-optical modulator.

21. Installation according to claim 1, wherein it comprises, downstream said pulse source (115), a means (3–5) for precompensation of the temporal dispersion of said pulses.

22. Installation according to claim 21, wherein said precompensation means (3–5) comprises an input coupling mirror (4) adapted to transmit said pulses to a set of two antiparallel prisms or gratings (5) and to transmit said precompensated pulses to an output coupling mirror (3).

23. Installation according to claim 1, wherein it comprises, downstream said pulse source (115), a polarization control means (8) adapted for controlling the polarization of said pulses.

24. Installation according to claim 23, wherein said polarization control means (8) comprises a λ/2 or λ/4 plate.

25. Installation according to claim 1, wherein it comprises, downstream said pulse source (115), a pulse shaping means (9).

26. Installation according to claim 25, wherein said pulse shaping means (9) comprises a divergent lens and a convergent lens, defining a two-element telescope.

27. Installation according to claim 1, wherein said focusing means (12–14) and directing means (22,40,53) are parts of a non invasive microscope or a macroscope.

28. Installation according to claim 27, wherein it comprises support means (60) for maintaining the material in a fixed position.

29. Installation according to claim 28, wherein it comprises positioning means (20) able to move said support means (60) relatively to said focusing means (12–14), in order said pulses be locally focused in said material chosen area.

30. Installation according to claim 29, wherein said positioning means (20) comprises an XYZ translation stage (20) moved by a motor and/or piezoactuators, said support means (60) is a material holder mounted on said translation stage.

31. Installation according to claim 28 or 29, wherein said support means (60) is a plate adapted to support at least a part of a human or animal patient.

32. Installation according to claim 28, wherein said support means (60) is adapted to a trans-illumination mode in which said pulses are directed on a first face of said material (19) and said response photons are collected at least downstream a second face of said material, opposite to said first face.

33. Installation according to claim 1, wherein said focusing means and directing means are parts of an endoscope.

34. Installation according to claim 33, wherein said directing means, said collecting means and said focusing means are enclosed in a movable head assembly (216;217;218).

35. A method for multi-dimensional laser scanning of a material comprising intrinsic chromophores responsive to excitation by photons of at least one chosen energy to produce response photons, said method comprising:

producing time stamp pulses of synchronized photons, locally focusing said pulses on a material to cause said intrinsic chromophores of said material to absorb groups of at least two synchronized photons to produce response photons, directing said response photons to at least one collecting zone, collecting said response photons in said at least one collecting zone, whatever the energy, converting said collected photons into data at least representative of their number, and storing said data in correspondence with at least the time stamp pulses that cause said material to produce said response photons, scanning said pulses through a chosen area of said material, and delivering from said data stored an image representative of said chosen area of said material, with a sub-millimeter resolution, and as function of their respective time stamp pulses.

36. Method according to claim 35, wherein said collected photons are converted into data representative of their respective arrival time, and stored in correspondence with at least a time stamp pulses and an arrival time.

37. Method according to claim 35 or 36, wherein said collected photons are converted into data representative of their respective energy, and stored in correspondence with at least a time stamp pulses and an energy.

38. Use of the method according to claim 35, for endoscopy, microscopy or macroscopy.

39. Use of the method according to claim 38, for providing information about a tissular or cellular structure and metabolism to monitor a surgical procedure.

40. Use of the method according to claim 39, for guiding the position of a laser in a laser-based procedure.

41. Use of the method according to claim 40, for guiding the excitation laser source in a laser ablation.

42. Use of the method according to claim 38, for providing information for following long term monitoring treatment effects and recovery.

43. Use of the method according to claim 38, for imaging in situ or ex situ biological material of human, animals, plants or prokaryotes, bic-synthetic tissues or chimeric tissues, artificial organs, genetically engineered elements, implanted xenogenic or autologous living or fixed tissue structures.

44. Use of the method according to claim 43, for the optical detection of cancer, metabolic or infectious diseases, foreign microorganisms, foreign particles or pathologies.

45. Use of the method according to claim 43, for imaging in situ or ex situ biological material of human skin or human mucosa.

46. Use of the method according to claim 45, for colposcopy, dermatology or oral cavities investigations.

47. Use of the method according to claim 43, for ophtalmoscopy.

48. Use of the method according to claim 43, for forensic detection or drug abuse detection.

49. Use of the method according to claim 43, for localization of drugs in pharmacology or pharmacodynamics.

50. Use of the method according to claim 43, for localization of gene product, cell proliferation and tissue modification in gene therapy.

51. Use of the method according to claim 43, for investigation of animal diseases and animal models of human diseases.

* * * * *